(12) United States Patent
Gavas et al.

(10) Patent No.: US 12,002,568 B2
(45) Date of Patent: Jun. 4, 2024

(54) ANALYZING EFFECT OF A SECONDARY COGNITIVE LOAD TASK ON A PRIMARY EXECUTIVE TASK

(71) Applicant: Tata Consultancy Services Limited, Mumbai (IN)

(72) Inventors: Rahul Dasharath Gavas, Kolkata (IN); Debatri Chatterjee, Kolkata (IN); Aniruddha Sinha, Kolkata (IN); Sanjoy Kumar Saha, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 718 days.

(21) Appl. No.: 16/662,797

(22) Filed: Oct. 24, 2019

(65) Prior Publication Data
US 2020/0135325 A1   Apr. 30, 2020

(30) Foreign Application Priority Data

Oct. 26, 2018   (IN) .............................. 201821040566

(51) Int. Cl.
*A61B 3/113* (2006.01)
*A61B 3/02* (2006.01)
(Continued)

(52) U.S. Cl.
CPC .............. *G16H 20/70* (2018.01); *A61B 3/113* (2013.01); *A61B 5/162* (2013.01); *A61B 5/163* (2017.08); *G06F 7/588* (2013.01); *A61B 5/168* (2013.01)

(58) Field of Classification Search
CPC ......... A61B 3/02; A61B 3/102; A61B 3/1025; A61B 3/1015; A61B 3/1225
See application file for complete search history.

(56) References Cited

U.S. PATENT DOCUMENTS

| 7,344,251 B2 * | 3/2008 | Marshall ................ G06V 40/19 351/210 |
| 9,940,844 B2 | 4/2018 | Gazzaley |
| 2016/0262680 A1 | 9/2016 | Martucci et al. |

FOREIGN PATENT DOCUMENTS

CN    110811645 A  *  2/2020

OTHER PUBLICATIONS

John N. Towse et al., "Analyzing human random generation behavior: A review of methods used and a computer program for describing performance", Dec. 1, 1998, Behavior Research Methods, Instruments and Computers, pp. 1-116 (Year: 1998).*

(Continued)

*Primary Examiner* — Dawayne Pinkney
(74) *Attorney, Agent, or Firm* — FINNEGAN, HENDERSON, FARABOW, GARRETT & DUNNER LLP

(57) ABSTRACT

This disclosure relates to analyzing effect of a secondary cognitive load task on a primary executive task. Human random sequence generation is a marker to study cognitive functions and inability to generate random sequences (RS) can reveal underlying impairments. Traditionally, 'call out' or 'write down' procedures are used to obtain human generated numbers, wherein short term memory and number of previously generated entities visible to a subject plays a major role. Also precise trial-wise or response-wise analysis may not be possible. In the present disclosure, the human generated random numbers are digitized into RS and a cognitive load (CL) inducing task is imposed on the executive task. The CL demanding task disrupts randomization performance. Deviation from randomness, load index based on gaze data and deviation from pupillometry data of healthy subjects are provided as indicators of an interference (Continued)

effect imposed by the CL and thereby indicative of underlying impairments.

10 Claims, 6 Drawing Sheets

(51) Int. Cl.
*A61B 3/10* (2006.01)
*A61B 3/12* (2006.01)
*A61B 5/16* (2006.01)
*G06F 7/58* (2006.01)
*G16H 20/70* (2018.01)

(56) References Cited

OTHER PUBLICATIONS

Cooper, R.P. "Cognitive Control in the Generation of Random Sequences: A Computational Study of Secondary Task Effects," *Proceedings of the Annual Meeting of the Cognitive Science Society*, Jul. 20-23, 2011, Boston, Massachusetts; pp. 2168-2173.

Oomens, W. et al. (Jun. 2015). "A time series approach to random number generation: using recurrence quantification analysis to capture executive behavior," *Frontiers in Human Neuroscience*; pp. 1-8.

Schulz, M-A. et al. (Jul. 2012). "Analysing Humanly Generated Random Number Sequences: A Pattern-Based Approach," *PLoS ONE*, vol. 7, No. 7; pp. 1-7.

\* cited by examiner

ANALYZING EFFECT OF A SECONDARY COGNITIVE LOAD TASK ON A PRIMARY EXECUTIVE TASK

PRIORITY CLAIM

This U.S. patent application claims priority under 35 U.S.C. § 119 to: Indian Patent Application No. 201821040566, filed on 26 Oct. 2018. The entire contents of the aforementioned application are incorporated herein by reference.

TECHNICAL FIELD

The disclosure herein generally relates to screening of mental impairments and cognitive dysfunctions, and, more particularly, to systems and computer implemented methods for analyzing effect of a secondary cognitive load task on a primary executive task.

BACKGROUND

Studies pertaining to probabilistic learning, gambling behavior and subjective probability have shown that successive responses in experimental settings are mutually dependent. This behavior is attributed to the concepts of 'subjective chance' or 'subjective randomness'. Clinical psychologists have been using these concepts for diagnosis of neurotics. Random sequence generation task has been used in building theoretical cognitive models for assessing neuropsychological characteristics of patients with multiple sclerosis, Parkinson's disease, Alzheimer's disease, survivors of traumatic closed-head injury and the like.

Most of the existing work involve 'call out' or 'write down' procedures to generate random number sequences. These two modes differ in the availability of previously generated, i.e. 'call out' items that have been spoken, can be remembered while the written responses are visible till the page is turned. The non-randomness of the generated sequences is attributed to the limited span of the short term memory and hence the number of previously generated entities visible to the participant plays a major role in this regard. Also, precise trial-wise or response-wise analysis may not be feasible with these approaches.

SUMMARY

Embodiments of the present disclosure present technological improvements as solutions to one or more of the above-mentioned technical problems recognized by the inventors in conventional systems.

In an aspect, there is provided a processor implemented method for assigning, by one or more hardware processors, a primary executive task to a subject, wherein the primary executive task is random number generation by the subject to obtain human generated random numbers; digitizing, by the one or more hardware processors, the human generated random numbers into a random sequence (RS) in baseline by concatenating the human generated random numbers until a predetermined number of random numbers is captured or random numbers in a predetermined time period is captured, wherein the RS in baseline is generated after a first predetermined baseline period; generating a random sequence in low load (LL) and a random sequence in high load (HL), by imposing, by the one or more hardware processors, a secondary cognitive load task in the form of a low cognitive load inducing task and a high cognitive load inducing task respectively, on the subject, wherein the RS in LL and the RS in HL are preceded by a pause for a second predetermined baseline period and a third predetermined baseline period respectively, to allow the subject to relax; receiving, by the one or more hardware processors, gaze data and pupillometry data associated with the subject, from an eye tracker, when the primary executive task and the secondary cognitive load task are being performed by the subject; extracting gaze related fixation patterns, by the one or more hardware processors, from the gaze data using a velocity based method that separates fixation points and saccade points in the gaze data based on point-to-point velocities thereof, wherein points having velocity below a predetermined threshold are fixation points, else the points are saccade points; and computing, by the one or more hardware processors, a load index (A) based on summation of length of each repeating fixation extracted from the gaze data, the predetermined number of random numbers captured and the total number of fixations from the gaze data, wherein the load index is indicative of the effect of the secondary cognitive load task on the primary executive task and wherein higher the value of the load index, higher is the effect of the secondary cognitive load task.

In another aspect, there is provided a system comprising: one or more data storage devices operatively coupled to one or more hardware processors and configured to store instructions configured for execution by the one or more hardware processors to: assign a primary executive task to a subject, wherein the primary executive task is random number generation by the subject to obtain human generated random numbers; digitize the human generated random numbers into a random sequence (RS) in baseline by concatenating the human generated random numbers until a predetermined number of random numbers is captured or random numbers in a predetermined time period is captured, wherein the RS in baseline is generated after a first predetermined baseline period; generate a random sequence in low load (LL) and a random sequence in high load (HL), by imposing a secondary cognitive load task in the form of a low cognitive load inducing task and a high cognitive load inducing task respectively, on the subject, wherein the RS in LL and the RS in HL are preceded by a pause for a second predetermined baseline period and a third predetermined baseline period respectively, to allow the subject to relax; receive gaze data and pupillometry data associated with the subject, from an eye tracker, when the primary executive task and the secondary cognitive load task are being performed by the subject; extract gaze related fixation patterns from the gaze data using a velocity based method that separates fixation points and saccade points in the gaze data based on point-to-point velocities thereof, wherein points having velocity below a predetermined threshold are fixation points, else the points are saccade points; and compute a load index (A) based on summation of length of each repeating fixation extracted from the gaze data, the predetermined number of random numbers captured and the total number of fixations from the gaze data, wherein the load index is indicative of the effect of the secondary cognitive load task on the primary executive task and wherein higher the value of the load index, higher is the effect of the secondary cognitive load task.

In yet another aspect, there is provided a computer program product comprising a non-transitory computer readable medium having a computer readable program embodied therein, wherein the computer readable program, when executed on a computing device, causes the computing device to: assign a primary executive task to a subject, wherein the primary executive task is random number generation by the subject to obtain human generated random numbers; digitize the human generated random numbers into a random sequence (RS) in baseline by concatenating the human generated random numbers until a predetermined number of random numbers is captured or random numbers in a predetermined time period is captured, wherein the RS in baseline is generated after a first predetermined baseline period; generate a random sequence in low load (LL) and a random sequence in high load (HL), by imposing a secondary cognitive load task in the form of a low cognitive load inducing task and a high cognitive load inducing task respectively, on the subject, wherein the RS in LL and the RS in HL are preceded by a pause for a second predetermined baseline period and a third predetermined baseline period respectively, to allow the subject to relax; receive gaze data and pupillometry data associated with the subject, from an eye tracker, when the primary executive task and the secondary cognitive load task are being performed by the subject; extract gaze related fixation patterns from the gaze data using a velocity based method that separates fixation points and saccade points in the gaze data based on point-to-point velocities thereof, wherein points having velocity below a predetermined threshold are fixation points, else the points are saccade points; and compute a load index (A) based on summation of length of each repeating fixation extracted from the gaze data, the predetermined number of random numbers captured and the total number of fixations from the gaze data, wherein the load index is indicative of the effect of the secondary cognitive load task on the primary executive task and wherein higher the value of the load index, higher is the effect of the secondary cognitive load task.

In accordance with an embodiment of the present disclosure, the one or more processors are further configured to digitize the human generated random numbers by: positioning a fixational cross '+' at the center of a white screen for the first predetermined baseline period; displaying digits (1-9) of a predetermined font size in a 3×3 matrix on the white screen; and concatenating the human generated random numbers generated based on randomly clicked digits on the white screen by the subject, till the predetermined number of random numbers is captured or random numbers in the predetermined time period is captured.

In accordance with an embodiment of the present disclosure, the secondary cognitive load task involves auditory addition.

In accordance with an embodiment of the present disclosure, the second predetermined baseline period and the third predetermined baseline period are equal.

In accordance with an embodiment of the present disclosure, the $$\text{load index}(A) = \frac{\left(\frac{\text{summation of length of each repeating fixation}*}{\text{total length of the random sequence}}\right)}{(\text{total number of fixations})}.$$

In accordance with an embodiment of the present disclosure, the one or more processors are further configured to perform one or more of: computing a deviation from randomness of the RS in baseline, the RS in LL and the RS in HL using one or more metrics including Coupon ($C_n$) test, Gap ($G_p$) test, Poker ($P_k$) test, Repetitions ($R_p$), Series ($S_r$), Variance of digits (VD), Diagram repetitions (DR), Cluster Ratio (CR), Random Number Generator (RNG), Turning Point index (TP), wherein the deviation from randomness is indicative of the effect of the secondary cognitive load task on the primary executive task and wherein higher the deviation from randomness, higher is the effect of the secondary cognitive load task; and comparing the received pupillometry data of the subject with the pupillometry data of healthy subjects to analyze the effect of the secondary cognitive load task on the primary executive task, wherein a deviation from the pupillometry data of healthy subjects is indicative of the effect of the secondary cognitive load task on the primary executive task.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
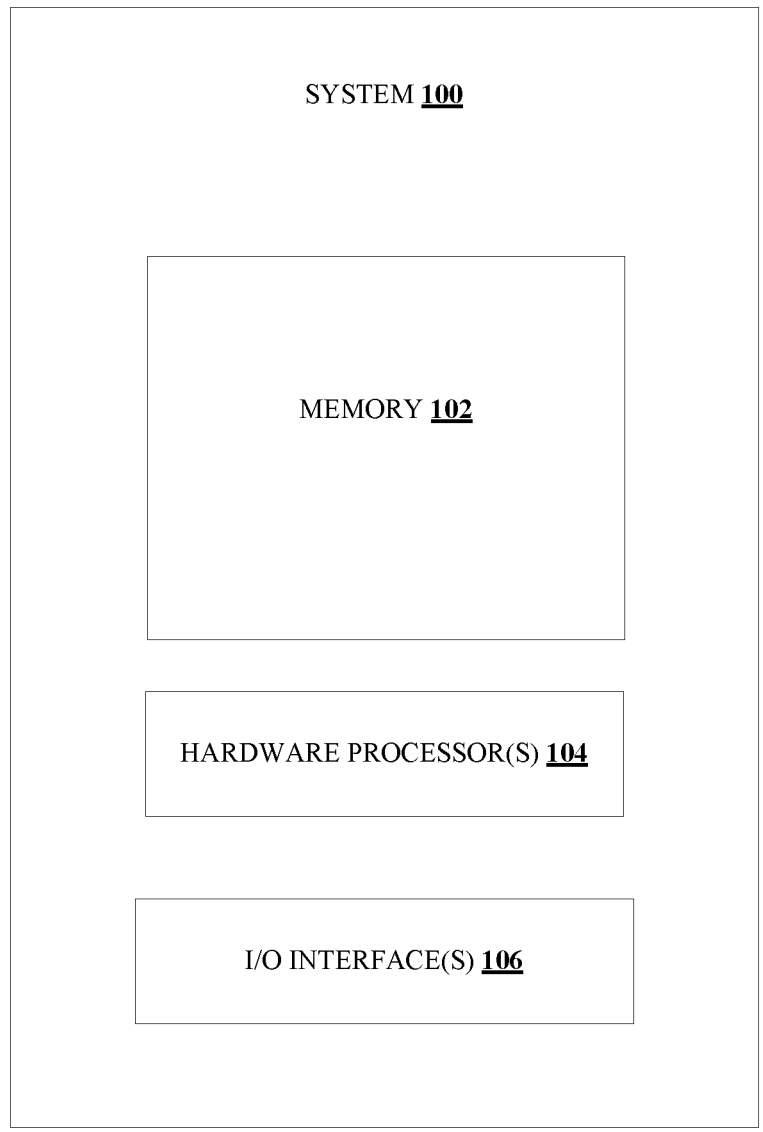
FIG. 1 illustrates an exemplary block diagram of a system for analyzing effect of a secondary cognitive load task on a primary executive task, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Complete Description of Embodiments

Executive functions are vital aspects of human behavior as they coordinate information, schedule actions and control attention. Human random sequence generation is a crucial marker to study cognitive functions. This is mainly due to the fact that it involves a lot of executive functioning and the inability to generate random sequences can reveal a lot about underlying mental impairments, if any. Traditionally used approaches involve 'call out' or 'write down'. Both these approaches have limitations due to the limited span of the short term memory of subjects being assessed. Again the information derivable from these approaches includes time taken to complete the assessment and accuracy of the generated random sequences which may not facilitate precise evaluation of cognitive dysfunctions across various ages for various medical conditions.

In accordance with the present disclosure, the random sequence generation task is digitized using mouse click events to overcome the traditional approaches. Again digitization also facilitates trial-wise or response-wise analyses not feasible in the traditional approaches. Consequently, inclusion of physiological sensing for cognitive behavior of the subjects in the form of gaze data and pupillometry data is also facilitated.

In accordance with the present disclosure, a cognitive load inducing task is paired with an established executive task resulting in a dual-task paradigm. The study of the generation of random sequences under the influence of cognitive load is required in order to well understand the executive functions subjected to memory workload. The executive task is performed both separately and concurrently. The comparisons of single and the dual tasks showed that the cognitive load demanding task disrupted randomization performance which led to the responses being less random since the executive-level tasks rely on the same attentional resources used by cognitive-load demanding tasks. This fact is supported by a metric called load index provided in the present disclosure, which may be used to analyze the effect of a secondary cognitive load task on a primary executive task. Physiological changes owing to gaze behavior of the subject also provide more insights of the underlying phenomenon of human random sequence generation. Results provided in the present disclosure confirm the interference effect imposed by the cognitive load demanding task on the random sequence generation task.

The present disclosure particularly analyzes the impact of attentional resources subjected to cognitive load. Accordingly, the subjects are made to attend to a standard executive task like random sequence (RS) generation while performing a concurrent mental addition task of varying difficulty levels. Experiments involving cases where the subject is needed to perform two types of tasks simultaneously have been considerably explored by cognitive psychologists to exclusively study the dynamics of attention deployment, competing task demands and the specialization of memory resources. There are also studies on the interference of the RS generation task over other primary task in order to characterize the interference effect as a competition for acquiring the attentional resources. Most of the studies on the interference effect have treated the secondary RS task as just a distractor to divert the subject's attention from the primary task. Hence, such studies typically may not measure the performance in the RS task which involves free will of the subject as against a cognitive load task. Therefore, in accordance with the present disclosure, a cognitive load (CL) task is used as a distractor (secondary task) from the RS task (primary task) to analyze effect of the secondary cognitive load task on the primary executive task. When a subject is incapable of dealing with all the information which is supposed to be processed per unit time then a deficit in terms of divided attention may be said to be prevalent and the analyzed effect may serve as a marker for screening of mental impairments and cognitive dysfunctions across various ages and for various medical conditions.

Referring now to the drawings, and more particularly to FIG. 1 through FIG. 6, where similar reference characters denote corresponding features consistently throughout the figures, there are shown preferred embodiments and these embodiments are described in the context of the following exemplary system and/or method.

FIG. 1 illustrates an exemplary block diagram of a system 100 for analyzing effect of a secondary cognitive load task on a primary executive task in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2A:
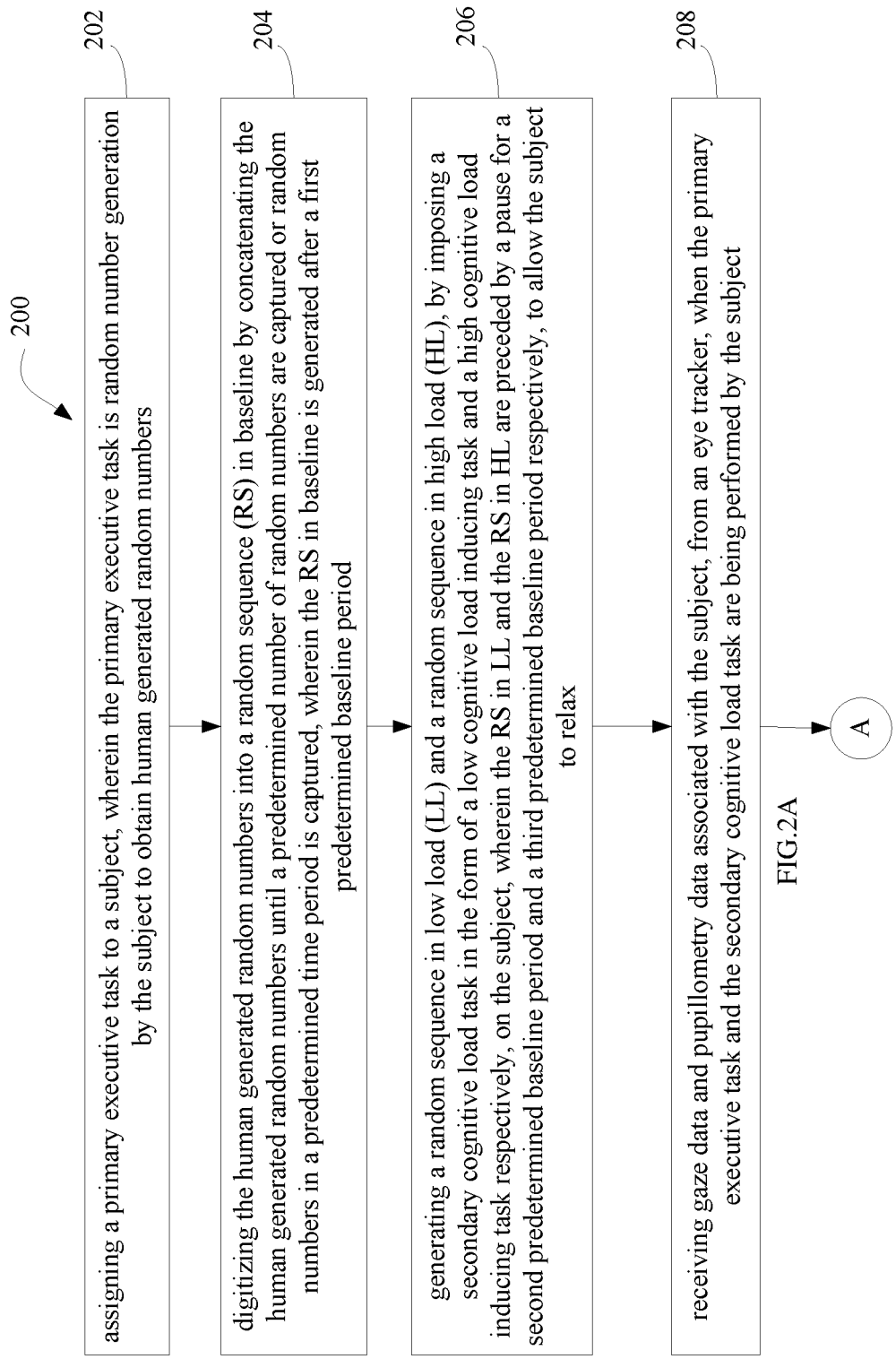
FIG. 2A and FIG. 2B illustrates an exemplary flow diagram of a computer implemented method for analyzing effect of a secondary cognitive load task on a primary executive task, in accordance with an embodiment of the present disclosure.
Figure 2B:
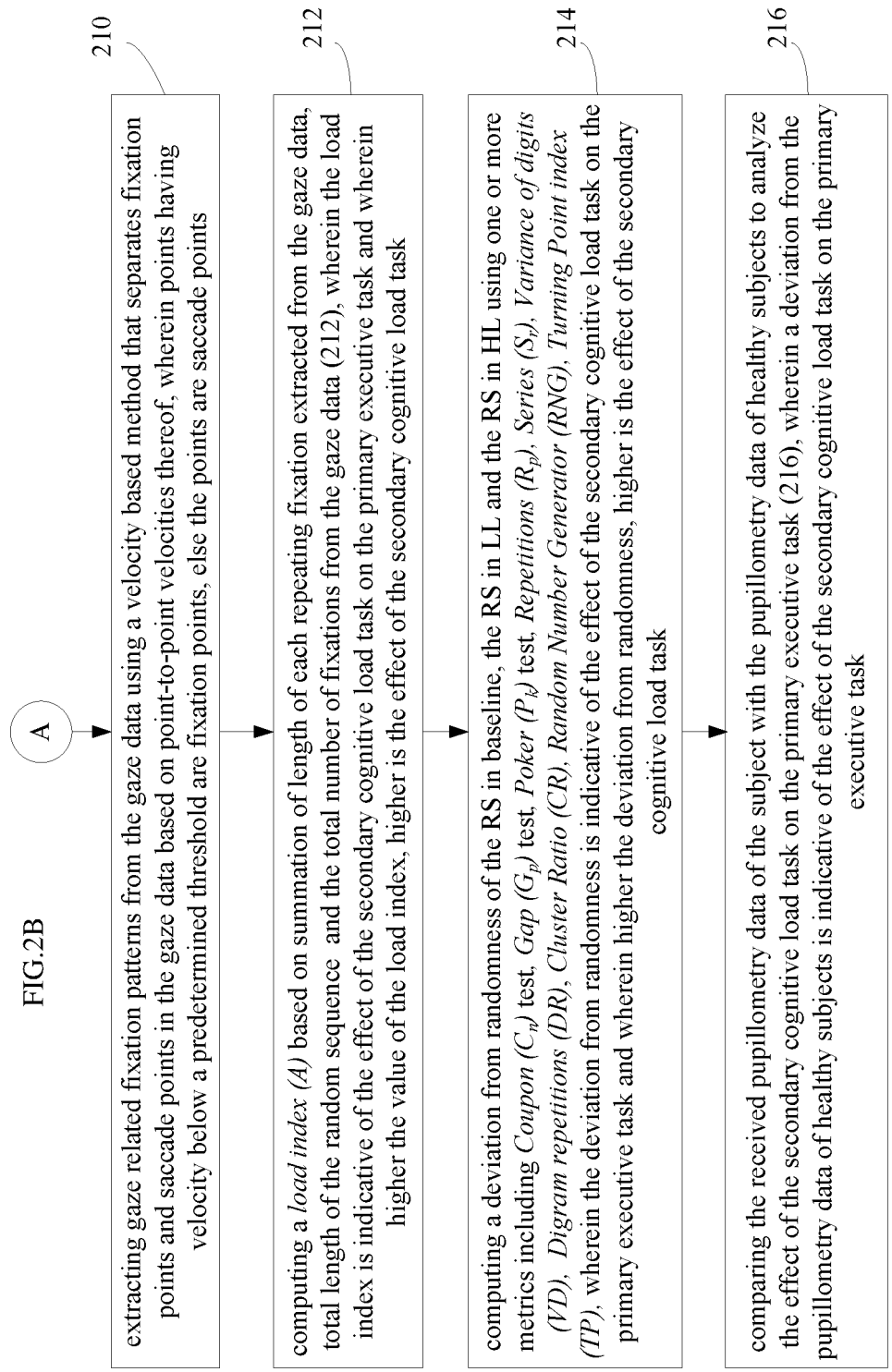

FIG. 2 illustrates an exemplary flow diagram for a computer implemented method 200 for analyzing effect of a secondary cognitive load task on a primary executive task, in accordance with an embodiment of the present disclosure. In an embodiment, the system 100 includes one or more data storage devices or memory 102 operatively coupled to the one or more processors 104 and is configured to store instructions configured for execution of steps of the method 200 by the one or more processors 104. The steps of the method 200 will now be explained in detail with reference to the components of the system 100 of FIG. 1. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

In accordance with the present disclosure, a cognitive load (CL) task serves as a stimulus on random sequence (RS) generation task. Firstly, the RS generation task is digitized and is coupled with an auditory addition task which is a standard CL inducing task.

In accordance with an embodiment of the present disclosure, the one or more processors 104 are configured to assign, at step 202, a primary executive task to a subject, wherein the primary executive task is random number generation by the subject to obtain human generated random numbers. Further the one or more processors 104 are configured to digitize, at step 204, the human generated random numbers into an RS in baseline by concatenating the human generated random numbers until a predetermined number of random numbers is captured or random numbers in a predetermined time period is captured, wherein the RS in baseline is generated after a first predetermined baseline period. In an embodiment, the predetermined number may be 50 and the first predetermined baseline period may be 30 seconds.

Figure 3:
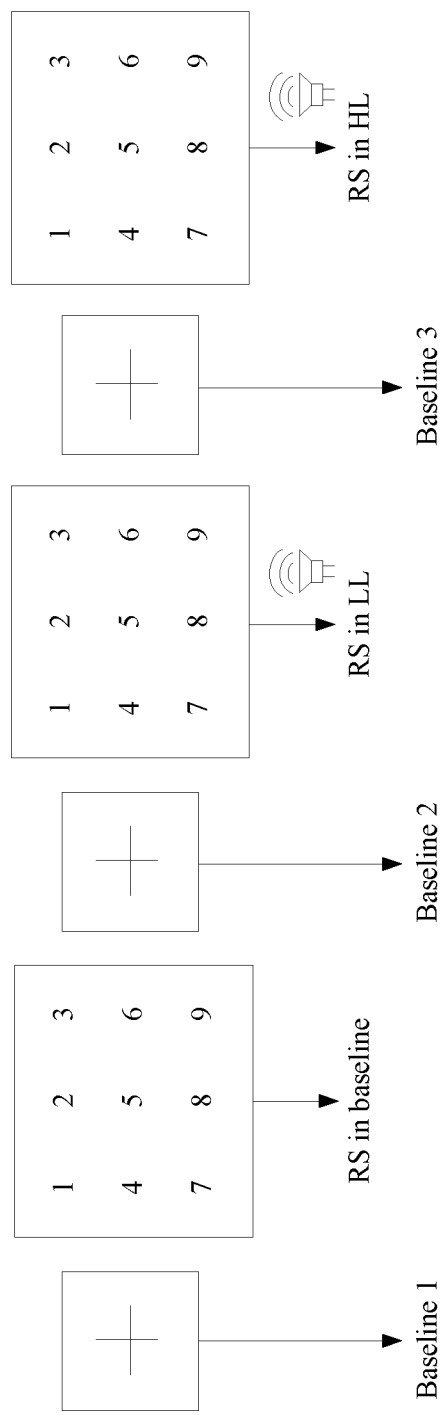
FIG. 3 illustrates design of a stimulus for analyzing effect of a secondary cognitive load task on a primary executive task, in accordance with an embodiment of the present disclosure.

FIG. 3 illustrates design of a stimulus for analyzing effect of the secondary cognitive load task on the primary executive task, in accordance with an embodiment of the present disclosure. In an embodiment, during the first predetermined baseline period of say 30 seconds, a fixational cross '+' is positioned at the center of a white screen serving as a baseline screen. Then the RS generation task is initiated wherein digits (1-9) of a predetermined font size are displayed in a 3×3 matrix on the white screen. In an embodiment, the predetermined font size may be 48 based on a pilot trial considering subjects viewing the stimulus at a distance of approximately 60 cm from the screen. The subject is expected to click on the nine numbers randomly. In an embodiment, the one or more processors 104 are configured to concatenate the human generated random numbers that are generated when the digits displayed on the white screen are randomly clicked by the subject till the predetermined number of random numbers (say 50) are captured. The RS generated after the 50 clicks form the RS in baseline.

The baseline screen is again displayed for a second predetermined baseline period to allow the subject to relax. In an embodiment, the second predetermined baseline period may be 30 seconds. The RS generation task is again presented to the subject. However, the primary task is now imposed with a secondary cognitive load (CL) inducing task which may be of low level (LL) or high level (HL). In an embodiment, the secondary cognitive load task involves auditory addition. In an embodiment, for a low CL inducing task, auditory digits 1 or 5 may be presented and for the high CL inducing task, auditory digits 1 through 9 may be presented. The subject is expected to add all the auditory digits presented, when performing the RS generation task, and report at the end of the trial. In an embodiment, the auditory digits may be presented at a rate of 1 digit per 3 seconds for the low load case and 1 digit per 4 seconds for the high load case. The trial lasts till the predetermined number of random numbers is captured (or random numbers in a predetermined time period is captured). In the exemplary embodiment under consideration, the trial lasts till say 50 clicks are captured. Accordingly, in an embodiment, the one or more processors 104 are configured to generate the RS sequence as an RS in LL and an RS in HL, at step 206, depending on the secondary CL task assigned. If the low CL inducing task was assigned first, the high CL inducing task is assigned after a third predetermined baseline period when the subject is allowed to relax and vice versa. In an embodiment, the third predetermined based line period may also be 30 seconds.

In accordance with an embodiment of the present disclosure, the one or more processors 104 are configured to receive, at step 208, gaze data and pupillometry data associated with the subject, from an eye tracker, when the primary executive task and the secondary cognitive load task are being performed by the subject. In accordance with an embodiment, the eye tracker is a wearable infrared sensor such as Eye Tribe™.

In accordance with an embodiment of the present disclosure, the one or more processors 104 are configured to extract gaze related fixation patterns, at step 210, from the gaze data using a velocity based method that separates fixation points and saccade points in the gaze data based on associated point-to-point velocities, wherein points having velocity below a predetermined threshold are fixation points, else the points are saccade points. In accordance with the present disclosure, fixations are extracted from each of the three scenario outputs—the RS in baseline, the RS in LL and the RS in HL. The predetermined number of random numbers captured or the mouse click events logged serve as ground truth sequence.

In accordance with an embodiment of the present disclosure, the one or more processors 104 are configured to compute, at step 212, a load index (A) based on summation of length of each repeating fixation extracted from the gaze data, the total length of the random sequence (or the ground truth sequence) and the total number of fixations from the gaze data. The load index (A) may be represented as shown below $$\text{load index}(A) = \frac{\left(\dfrac{\text{summation of length of each repeating fixation} *}{\text{total length of the random sequence}}\right)}{(\text{total number of fixations}) \rightarrow} \quad (1)$$

In the exemplary embodiment under consideration, the ground truth sequence for each three scenarios comprises 50 mouse clicks. As the CL increases, additional mental resources are required for the subject to perform the secondary CL task of addition. With the increase in CL, the number of consecutive fixations around a particular number increases and is referred as repeating fixations. Table I below represents sample fixations (extracted from the gaze data) mapped onto numbers for each of the three scenarios, wherein summation of length of each repeating fixation is 2 for the RS in baseline, 6 for the RS in LL and 9 for the RS in HL.

TABLE I

| RS in baseline | RS in LL | RS in HL |
|---|---|---|
| 1→2→6→8→4→ | 3→3→2→1→6→ | 1→5→5→2→6→ |
| 7→4→3→5→1→ | 4→7→9→9→8→ | 6→7→7→7→8→ |
| 1→4→2→8→9 | 7→5→5→8→2 | 4→3→3→2→1 |

Table I shows the first 15 fixation sequences (mapped onto the 9 numbers on the screen) obtained for a particular subject, the repeating fixations being highlighted in bold text. The number of repetitions is expected to be higher for the HL case and minimum for the baseline period. Hence, from equation (1) it is clear that as the interference of the secondary task and the CL increases, the value of the load index (A) increases. For the RS in baseline, it is expected to be least and maximum when subjected to HL task. Thus, the fixations extracted from gaze data enable computing the load index (A) that is indicative of the effect of the secondary cognitive load task on the primary executive task, wherein higher the value of the load index, higher is the effect of the secondary cognitive load task. As against this, state-of-the art metrics for assessing randomness of the human generated random numbers is dependent on the actual RS generated by the subjects and cannot rely on physiological sensing because of the traditional approaches used.

It is difficult to use a single test to logically conclude randomness of a sequence, since, using direct observation based techniques to measure randomness is not possible. However, departures from randomness can be quantified. Hence, different metrics are essential to identify various patterns and order types in the given sequence. In accordance with the present disclosure, some state-of-the art metrics used are as follows:

(i) Coupon ($C_n$) test: The number of responses that occurred before all the digits got emitted. The $C_n$ score is the mean of all complete sets (no. of responses generated before all the digits are used at least once).

(ii) Gap ($G_p$) test: The 'gap' or the number of entities between two occurrences of same digits. This yields a set of gaps for each number (1-9 in the exemplary embodiment under consideration). Gap score is the median of all the values.

(iii) Poker ($P_k$) test: The generated sequence is buffered in a window of length 5 and the $P_k$ score is the number of 'two-of-a-kind' elements amongst all the windows.

The metrics (i) through (iii) are computed directly from the obtained sequences. The rest of the features are computed from the (9×9) digram matrix constructed from the obtained responses.

(iv) Repetitions ($R_p$): This score is the sum of the values in the major diagonal of the digram matrix.

(v) Series ($S_r$): This is the sum of the values in diagonals above and below the major diagonal; plus the values in the cells (1,9) and (9,1)

(vi) Variance of digits (VD): This score is the variance of the marginal totals (vii) Digram repetitions (DR): Sum of the values in each cell minus one (viii) Cluster Ratio (CR): This refers to the variance of all the entries in the digram divided by the mean of the values (ix) Random Number Generator (RNG): A measure of departure from randomness that reflects the disproportion with which any number follows any other number in a given short sequence (x) Turning Point index (TP): This index is computed directly from the obtained sequence and is defined by the number of responses that mark a change between the ascending and descending sequences In accordance with an embodiment of the present disclosure, the one or more processors 104 are configured to compute, at step 214, a deviation from randomness of the RS in baseline, the RS in LL and the RS in HL using one or more of the state-of-the art metrics listed above, wherein the deviation from randomness is indicative of the effect of the secondary cognitive load task on the primary executive task such that higher the deviation from randomness, higher is the effect of the secondary cognitive load task.

In accordance with an embodiment of the present disclosure, the one or more processors 104 are configured to compare, at step 216, the pupillometry data of the subject with the pupillometry data of healthy subjects to analyze the effect of the secondary cognitive load task on the primary executive task, wherein a deviation from the pupillometry data of healthy subjects is indicative of the effect of the secondary cognitive load task on the primary executive task.

Experimental Results

Fifteen healthy subjects with mean age 25±4 years, participated in the study. All of them hailed from similar educational and cultural backgrounds. All of them were right handed and had normal or corrected to normal vision with glasses. Data collection was conducted on 2 different days. The sequence of the trial was: RS in baseline→RS in LL→RS in HL in case 1. After a gap of 1 day, the same subject performed RS in baseline→RS in HL→RS in LL for case 2. Case 1 and case 2 were counterbalanced between the subjects to eliminate effect of sequencing, i.e. 50% of the subjects performed case 1 on day 1 while the rest performed case 2 on day 1.

Figure 4:
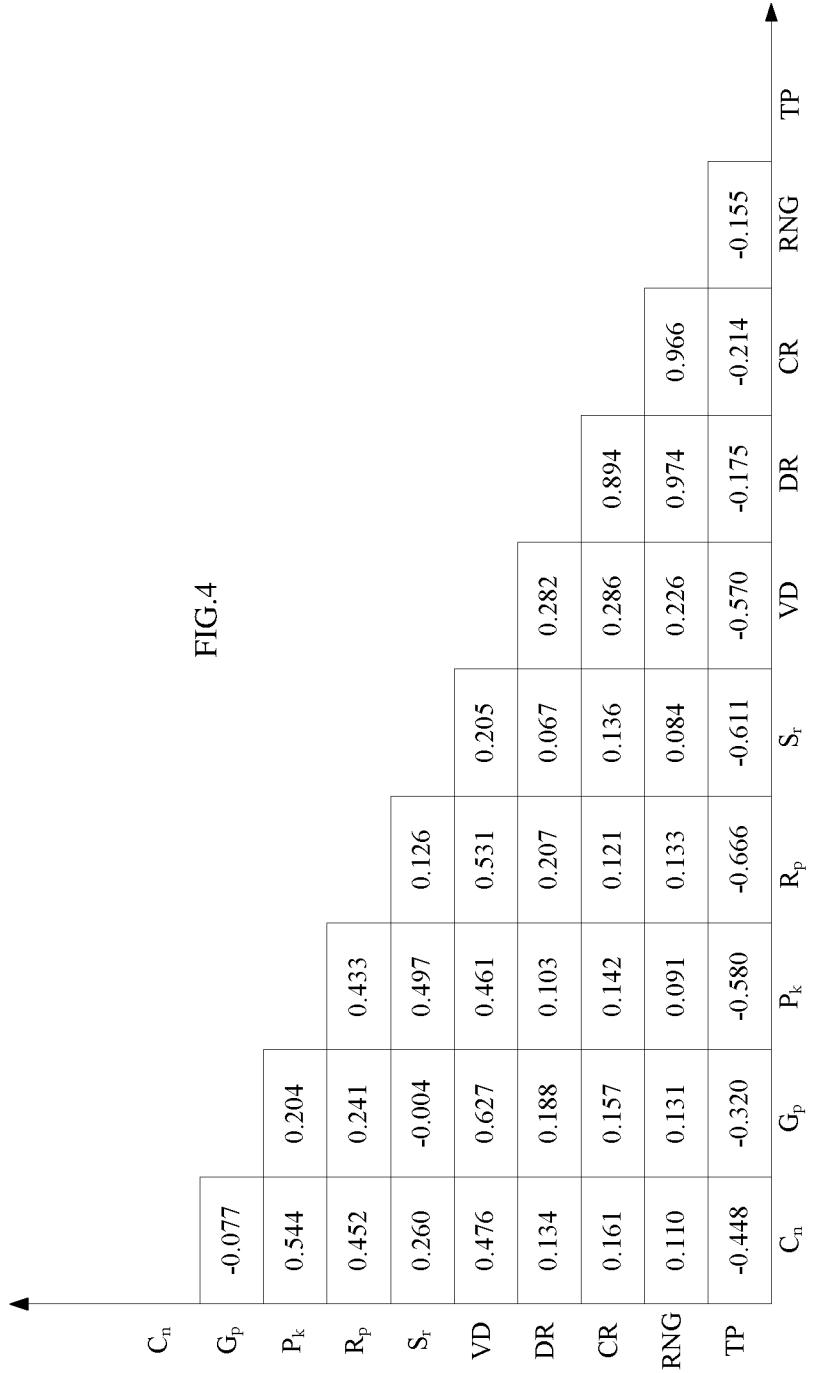
FIG. 4 illustrates Pearson correlations amongst a plurality of metrics for a random sequence in baseline, a random sequence in low load and a random sequence in high load for different task assignment cases taken together, in accordance with an embodiment of the present disclosure.

Inter-relationships among the metrics: To establish the validity of the digitization of the RS generation task performed in accordance with the present disclosure, the correlations among the different state-of-the-art metrics are compared against the metrics computed in accordance with the digitized RS of the present disclosure. FIG. 4 illustrates Pearson correlations amongst a plurality of metrics for the RS in baseline, the RS in LL and the RS in HL for the different task assignment cases (case 1 and case 2) taken together, in accordance with an embodiment of the present disclosure. The following inferences may be noted:

High correlation was obtained among the metrics of randomness, i.e. RNG and CR with a value of 0.966 which is comparable to the state of the art value of 0.95.

As known in the art, for the case of bias related metrics, no strong correlations were observed between them. It may be noted that in the art, the RS were generated orally and it was paced using a metronome.

As known in the art, positive correlations were observed in $R_p$ on RNG and CR.

Strong positive correlation was observed among VD and $G_p$ which is contradictory to the art. This may be attributed to the fact that the subjects undergoing the test in accordance with the present disclosure required generation of numbers between 1 and 9 whereas in the art, the range was from 0-9. This largely affects the metric $G_p$. Also, the test in accordance with the present disclosure required the generation of self-paced 50 random numbers using mouse clicks at a given instant, whereas the subjects in the art produced 100 numbers orally at a fixed pace.

Test-retest reliability: Test-retest was conducted to validate the reliability of the digitized RS generation task of the present disclosure. Hence the validation was carried out only on the RS in baseline scenario for case 1 and case 2.

TABLE II

Test - retest considering the baseline data in case 1 and case 2

|  | Correlation | p-value (probability) |
| --- | --- | --- |
| $C_n$ | 0.164 | 0.095 |
| $G_p$ | −0.071 | 0.17 |
| $P_k$ | 0.495 | 0.6 |
| $R_p$ | 0.73 | 0.24 |
| $S_r$ | 0.36 | 0.23 |
| VD | 0.243 | 0.97 |
| DR | 0.539 | 0.91 |
| CR | 0.464 | 0.44 |
| RNG | 0.499 | 0.67 |
| TP | 0.311 | 0.86 |

The following points were observed:
- Test-test reliability revealed positive correlations among all but one metric ($G_p$) for the RS in baseline scenario taken on two different days.
- The RNG index of 0.499 is comparable to the reliability correlation varying between 0.4 and 0.7 as known in the art.
- The p-values are all >0.05 indicating that the data are not significantly different. Among the metrics of bias, the highest correlation obtained was in case of $R_p$ followed by $S_r$.
- The decrease in correlation in $G_p$ suggests the deviation in the cycling nature of the generated sequences. The correlations of randomness metrics, i.e. RNG and CR are 0.499 and 0.464 indicating that randomness was unaffected in both the sessions (2 days in the exemplary embodiment).
- The test-retest was also conducted on the response times (time elapsed between successive clicks) for the RS in baseline scenario for the two different sessions (2 days in the exemplary embodiment) and the retest correlation value obtained was 0.8031.

The interference effect: The introduction of CL during the RS generation task has a significant impact on the nature of the generated RS as is evident in Table III.

that the generated sequences are comparatively more random in the baseline than while subjected to cognitive load task. The departures from randomness in the stimulus state immediately following the baseline is indicative of the interference effect posed by the cognitive load demanding task.

In case 1, the low load task followed the baseline random sequence task. The metrics, $R_p$, DR, CR, RNG are statistically significant with p<0.05 in each of them. It is to be noted that all the metrics of randomness (CR and RNG) and one metric from bias is distinguishing here. In case of baseline RS task and high load task in case 1, there are no statistically significant differences in the metrics. But in case of LL and HL RS tasks, $R_p$ again was a distinguishing factor with p<0.05. This shows that there is difference only in the baseline to the low load but not in baseline to the high load. This short term effect in randomness can be attributed to the interference effect.

Consider the case 2 wherein the HL task followed immediately after the baseline RS task. The metrics that are statistically significant with p<0.05 are DR, CR and RNG. An interesting observation here is, apart from baseline to HL, there are four other metrics that are statistically significant (p<0.05) in baseline to LL task

TABLE III

Expected and obtained values of various metrics (averaged across subjects) for human RS task and pseudo-random number generator (PRNG). The values in LL and HL which varied significantly (p < 0.05) from their corresponding RS in baseline are shown in bold text.

| Metrics | Expected | Case 1 | | | Case 2 | | | PRNG |
|---|---|---|---|---|---|---|---|---|
| | | RS in baseline | RS in LL | RS in HL | RS in baseline | RS in HL | RS in LL | |
| $C_n$ | 25.46 | 15.26 | 14.31 | 15.67 | 13.22 | 15.8 | 16.23 | 25.60 |
| $G_p$ | 6.44 | 9.18 | 9.53 | 8.90 | 9.54 | 9.18 | 9.11 | 7.04 |
| $P_k$ | 7.68 | 2.53 | 1.47 | 1.80 | 2.27 | 1.47 | 1.67 | 4.87 |
| $R_p$ | 9 | 2.27 | 0.67 | 1.13 | 1.67 | 0.47 | 0.53 | 5.27 |
| $S_r$ | 18 | 13.40 | 13.33 | 14.73 | 12.07 | 15.2 | 12.87 | 10.87 |
| VD | 4.93 | 2.99 | 3.31 | 3.76 | 2.97 | 3.27 | 4.07 | 3.97 |
| DR | 15 | 15.33 | 17.31 | 17.53 | 15.40 | 18.27 | 19.87 | 12.8 |
| CR | 1.09 | 1.16 | 1.32 | 1.43 | 1.21 | 1.45 | 1.53 | 1 |
| RNG | 0.25 | 0.26 | 0.30 | 0.32 | 0.27 | 0.33 | 0.36 | 0.21 |
| TP | 100 | 87.50 | 83.13 | 80.63 | 88.33 | 86.88 | 84.38 | 86.67 |

The expected values of each of the metrics are computed as per the suggestions given by Ginsburg and Karpuik in "Random generation: Analysis of the responses," Perceptual and Motor Skills, vol. 79, no. 3, pp. 1059-1067, 1994. The last column in Table III corresponds to the results on the RS generated by Python's inbuilt pseudo-random number generator (PRNG). The PRNG was seeded with the subject's IDs for the sake of repeatability. Following are the observations from Table III:

Comparing the performance of the PRNG against the rest of the columns for the human generated RS supports the fact that humans are not good generators of random sequence which is also proposed by Figurska et al. in "Humans cannot consciously generate random numbers sequences: Polemic study," Medical hypotheses, vol. 70, no. 1, pp. 182-185, 2008. Also, a keen observation on the differences in the metric values from the baseline to the stimulus states reveals ($S_r$, DR, CR, RNG). This shows the prolonged effect of interference from HL to LL.

Evans reported an increase in RNG of 0.216 to 0.427 from the baseline random task to a stimulus based RS task in "Monitoring attention deployment by random number generation: An index to measure subjective randomness," Bulletin of the Psychonomic Society, vol. 12, no. 1, pp. 35-38, 1978. The stimulus used was the Stroop test. In the present test, it was found that RNG from baseline to LL was 0.26 to 0.3 (p=0.049) and then from 0.26 in baseline to 0.32 for the HL task (p=0.094) in case 1. For the case 2, the RNG varied from 0.27 to 0.33 in HL (p<0.05) and from 0.27 in baseline to 0.36 in the LL task (p=0.0061).

The obtained values in each of the cases are compared with the expected values using $\chi^2$ test and the results are given in Table IV.

TABLE IV

| | Chi-square statistic on the expected and the observed values | | | | | | |
|---|---|---|---|---|---|---|---|
| | Case 1 | | | Case 2 | | | |
| | RS in baseline | RS in LL | RS in HL | RS in baseline | RS in HL | RS in LL | PRNG |
| p-value | 0.044 | 0.0042 | 0.011 | 0.011 | 0.010 | 0.006 | 0.558 |
| $\chi^2$ | 17.252 | 24.048 | 21.264 | 21.278 | 21.51 | 22.987 | 7.755 |

In all of the cases, the scores obtained for the subjects varied significantly from the expected values with $p<0.05$, which is indicative of the fact that humans are not good random sequence generators as known in the art. In case of the values obtained for the PRNG, the scores did not vary significantly from the expected values ($p>0.05$), which shows that the used PRNG is a good generator of random sequences.

Figure 5:
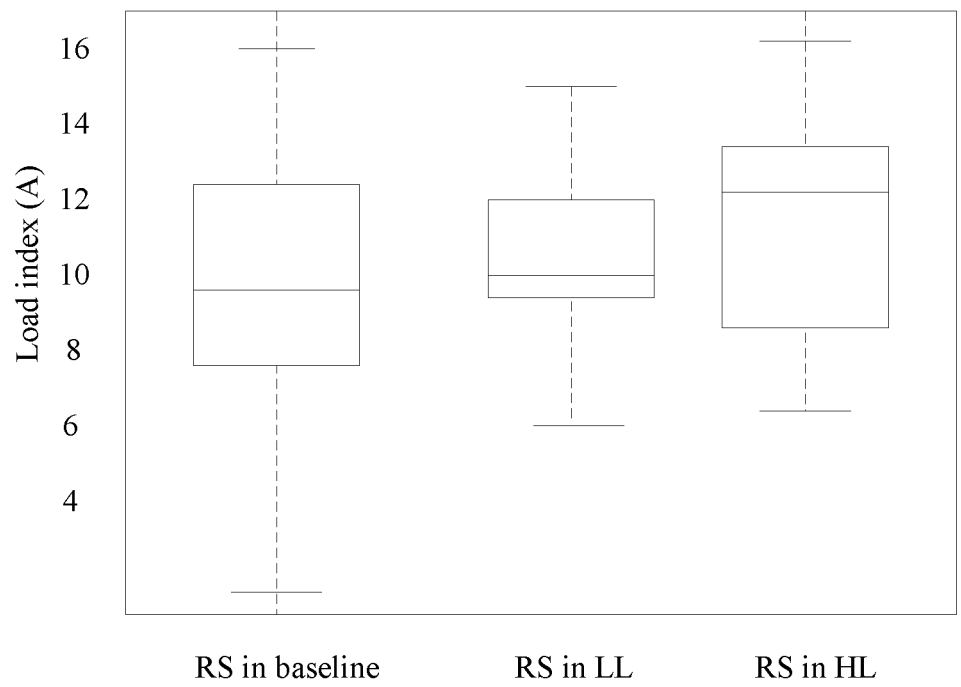
FIG. 5 illustrates load index values for a random sequence in baseline, a random sequence in low load and a random sequence in high load, in accordance with an embodiment of the present disclosure.

Results for load index (A): FIG. 5 illustrates load index values for an RS in baseline, an RS in LL and an RS in HL, in accordance with case 1 of the present disclosure. Similar results may be seen for case 2 as well. The average value of A increases from RS in baseline to the RS in LL and HL tasks as shown in FIG. 5. This shows that ambiguity is minimum in baseline, and increases with the increase in CL. Considering all the subjects, the average±SD time taken for the three scenarios (RS in baseline, RS in LL and RS in HL) for 50 clicks are 42.58±13.6, 42.42±13.27 and 42.45±10.77 seconds, respectively. It may be noted that the average duration spent in each task is similar and apparently they seem to have similar impact. However, upon the analyses of the gaze data, it was found that it not and hence the load index is a useful distinguishing measure in this regard.

Figure 6:
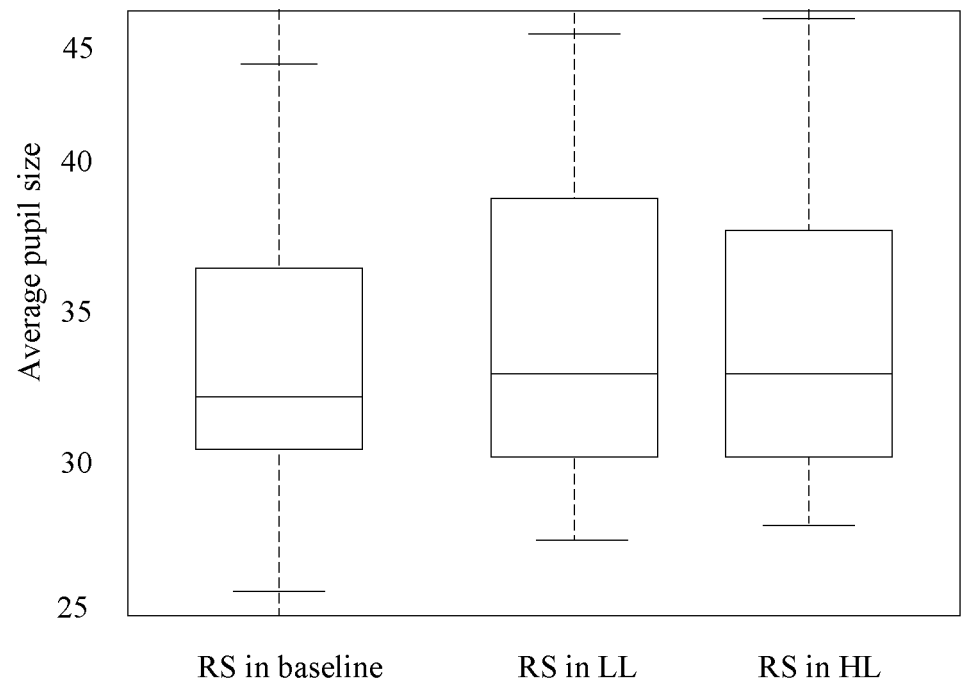
FIG. 6 illustrates average pupil size values for a random sequence in baseline, a random sequence in low load and a random sequence in high load for different task assignment cases taken together, in accordance with an embodiment of the present disclosure.

Further analysis on the pupillometry data shows that the average pupil size dilation increases from baseline to the load conditions as evident in FIG. 6 which illustrates average pupil size values for an RS in baseline, an RS in LL and an RS in HL for different task assignment cases (case 1 and case 2) taken together, in accordance with an embodiment of the present disclosure. It may be noted that the pupil size returned by the eye tracker is in arbitrary units. The variation in pupil size dilation under the influence of auditory CL is studied by Rahul Gavas et al. in "Estimation of cognitive load based on the pupil size dilation," in Systems, Man, and Cybernetics (SMC), 2017 IEEE International Conference on. IEEE, 2017. The present results are similar but with the inclusion of RS generation along with auditory CL stimulus. Thus the initial findings are in line with the impact of interference effects on the executive functionalities and any deviation from healthy subjects can serve as a marker to detect abnormalities, if any.

Thus systems and methods of the present disclosure analyze the effect of a secondary CL task on a primary executive task which is the generation of RS of numbers. Different state-of-the-art metrics have been used for checking the quality of RS generated under various CL conditions. The obtained results are straight-forward owing to the interference effect. The concurrent CL task interfered with the performance characteristics like the randomness and bias associated with the primary RS generation task. The initial findings with respect to the eye gaze and pupillometry serve as a good indicator of the performance of the executive functioning. A metric referred as the load index is provided for analyzing the effect of various CL conditions from the gaze data. Results show that the load index metric is a good distinguisher of CL and ambiguity of an individual. This can serve as a marker in early screening or diagnosis of cognitive impairments like Stroke, Dementia, Schizophrenia and Parkinson's disease.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method, comprising:
assigning, by one or more hardware processors, a primary executive task to a subject, wherein the primary executive task is generation of random numbers by the subject to obtain human generated random numbers;
digitizing, by the one or more hardware processors, the human generated random numbers into a first random sequence (RS) in a baseline by concatenating the human generated random numbers until:
capture of a specific number of the generated random numbers, or
capture of the generated random numbers in a specific time period, wherein
the first RS in the baseline is digitized after a first baseline period, and
the first baseline period is a time period after the generation of the random numbers;
generating, after the primary executive task, a second RS in a low load (LL) and a third RS in a high load (HL), by the one or more hardware processors, by imposing a secondary cognitive load task in a form of:
a low cognitive load inducing task on the subject, and
a high cognitive load inducing task on the subject, wherein
the secondary cognitive load task includes auditory addition of a plurality of auditory digits,
the low cognitive load inducing task includes the auditory addition of a plurality of first specific auditory digits of the plurality of auditory digits,
the high cognitive load inducing task includes the auditory addition of a plurality of second specific auditory digits of the plurality of auditory digits,
a count of the plurality of second specific auditory digits is greater than a count of the plurality of first specific auditory digits,
an auditory digit of the plurality of auditory digits is presented at a rate of 1 auditory digit per 3 seconds for the low cognitive load inducing task,
the auditory digit of the plurality of auditory digits is presented at a rate of 1 auditory digit per 4 seconds for the high cognitive load inducing task,
the low cognitive load inducing task is preceded by a first pause for a second baseline period, wherein the second baseline period is a time period after the digitization of the RS in the baseline,
the high cognitive load inducing task is preceded by a second pause for a third baseline period, wherein the third baseline period is a time period after completion of the low cognitive load inducing task, and
each of the second baseline period and the third baseline period allows the subject to relax;
receiving, by the one or more hardware processors, gaze data and pupillometry data associated with the subject, from an eye tracker, wherein each of the gaze data and the pupillometry data is specific data that is received during performance of both the primary executive task and the secondary cognitive load task by the subject;
extracting gaze related fixation patterns, by the one or more hardware processors, from the received gaze data by separating fixation points of the gaze data and saccade points of the gaze data based on point-to-point velocities in the gaze data, wherein
the fixation patterns are extracted for each of the first RS in the baseline, the second RS in the LL, and the third RS in the HL,
the fixation points include a plurality of points of the gaze data having a first velocity that is lesser than a specific threshold, and
the saccade points include a second plurality of points of the gaze data having a second velocity that is equal to or greater than the specific threshold; and
computing, for each of the first RS in the baseline, the second RS in the LL, and the third RS in the HL, by the one or more hardware processors, a load index (A) by calculating a ratio of:
a product of summation of a length of repeating fixation of the fixation patterns of the extracted gaze data and a total length of random sequence, and
a total number of fixations of the gaze data, wherein the load index indicates an effect of the secondary cognitive load task on the primary executive task, and
a value of the load index is directly proportional to the effect of the secondary cognitive load task on the primary executive task.

2. The processor implemented method of claim 1, wherein digitizing the human generated random numbers further comprises:
positioning a fixational cross '+' at a center of a white screen for the first baseline period;
displaying a plurality of digits of a specific font size in a 3×3 matrix on the white screen; and
concatenating the human generated random numbers based on randomly clicked digits of the plurality of displayed digits by the subject.

3. The processor implemented method of claim 1, wherein an interval of each of the first baseline period, the second baseline period, and the third baseline period is equal.

4. The processor implemented method of claim 1, further comprising:

computing a first deviation from randomness of the first RS in the baseline, the second RS in the LL, and the RS in the HL using one or more metrics, wherein the one or more metrics includes Coupon (Cn) test, a Gap (Gp) test, a Poker (Pk) test, a Repetitions (Rp), a Series (Sr), a Variance of digits (VD), a Digram repetitions (DR), a Cluster Ratio (CR), a Random a Number Generator (RNG), and a Turning Point index (TP), wherein
the first deviation indicates the effect of the secondary cognitive load task on the primary executive task, and
the first deviation is directly proportional to the effect of the secondary cognitive load task on the primary executive task; and
comparing the received pupillometry data of the subject with specific pupillometry data of a healthy subject to analyze the effect of the secondary cognitive load task on the primary executive task, wherein a second deviation from the specific pupillometry data indicates the effect of the secondary cognitive load task on the primary executive task.

5. A system, comprising:
one or more data storage devices operatively coupled to one or more hardware processors, wherein the one or more data storage devices configured to store instructions for execution by the one or more hardware processors to:
assign a primary executive task to a subject, wherein the primary executive task is generation of random numbers by the subject to obtain human generated random numbers;
digitize the human generated random numbers into a first random sequence (RS) in a baseline by concatenating the human generated random numbers until:
capture of a specific number of the generated random numbers, or
capture of the generated random numbers in a specific time period, wherein
the first RS in the baseline is digitized after a first baseline period, and
the first baseline period is a time period after the generation of the random numbers;
generate, after the primary executive task, a second RS in a low load (LL) and a third RS in a high load (HL), by imposing a secondary cognitive load task in a form of:
a low cognitive load inducing task on the subject, and
a high cognitive load inducing task on the subject, wherein
the secondary cognitive load task includes auditory addition of a plurality of auditory digits,
the low cognitive load inducing task includes the auditory addition of a plurality of first specific auditory digits of the plurality of auditory digits,
the high cognitive load inducing task includes the auditory addition of a plurality of second specific auditory digits of the plurality of auditory digits,
a count of the plurality of second specific auditory digits is greater than a count of the plurality of first specific auditory digits,
an auditory digit of the plurality of auditory digits is presented at a rate of 1 auditory digit per 3 seconds for the low cognitive load inducing task,
the auditory digit of the plurality of auditory digits is presented at a rate of 1 auditory digit per 4 seconds for the high cognitive load inducing task,
the low cognitive load inducing task is preceded by a first pause for a second baseline period, wherein the second baseline period is a time period after the digitization of the first RS in the baseline,
the are high cognitive load inducing task is preceded by a second pause for a third baseline period, wherein the third baseline period is a time period after completion of the low cognitive load inducing task, and
each of the second baseline period and the third baseline period allows the subject to relax;
receive gaze data and pupillometry data associated with the subject, from an eye tracker, wherein each of the gaze data and the pupillometry data is specific data that is received during performance of both the primary executive task and the secondary cognitive load task by the subject;
extract gaze related fixation patterns from the gaze data using by separating fixation points of the gaze data and saccade points of the gaze data based on point-to-point velocities, wherein
the fixation patterns are extracted for each of the first RS in the baseline, the second RS in the LL, and the third RS in the HL,
the fixation points include a plurality of points of the gaze data having a first velocity that is lesser than a specific threshold, and
the saccade points include a second plurality of points of the gaze data having a second velocity that is equal to or greater than the specific threshold; and
compute for each of the first RS in the baseline, the second RS in the LL, and the third RS in the HL, a load index (A) by calculating a ratio of:
a product of summation of a length of repeating fixation of fixation patterns of the extracted gaze data and a total length of random sequence, and
a total number of fixations of the gaze data, wherein
the load index indicates an effect of the secondary cognitive load task on the primary executive task, and
a value of the load index is directly proportional to the effect of the secondary cognitive load task on the primary executive task.

6. The system of claim 5, wherein the one or more hardware processors are further configured to digitize the human generated random numbers by:
positioning a fixational cross '+' at a center of a white screen for the first baseline period;
displaying a plurality of digits of a font size in a 3×3 matrix on the white screen; and
concatenating the human generated random numbers based on randomly clicked digits of the plurality of displayed digits by the subject.

7. The system of claim 5, wherein an interval of each of the first baseline period, the second baseline period and the third baseline period is equal.

8. The system of claim 5, wherein the one or more hardware processors are further configured to:
compute a first deviation from randomness of first RS in the baseline, the second RS in the LL, and the third RS in the HL using one or more metrics, wherein the one or more metrics includes including a Coupon (Cn) test, a Gap (Gp) test, a Poker (Pk) test, a Repetitions (CR), a Series (Sr), a Variance of digits (VD), a Digram repetitions (DR), a Cluster Ratio (CR), a Random a Number Generator (RNG), a Turning Point index (TP), wherein
the first deviation indicates the effect of the secondary cognitive load task on the primary executive task, and
the first deviation is directly proportional to the effect of the secondary cognitive load task on the primary executive task; and
compare the received pupillometry data of the subject with specific pupillometry data of a healthy subject to analyze the effect of the secondary cognitive load task on the primary executive task, wherein a second deviation from the specific pupillometry data indicates the effect of the secondary cognitive load task on the primary executive task.

9. A computer program product comprising a non-transitory computer readable medium having a computer readable program embodied therein, wherein the computer readable program, when executed on a computing device, causes the computing device to:
assign a primary executive task to a subject, wherein the primary executive task is generation of random numbers by the subject to obtain human generated random numbers;
digitize the human generated random numbers into a first random sequence (RS) in a baseline by concatenating the human generated random numbers until:
capture of a specific number of the generated random numbers, or
capture of the generated random numbers in a specific time period, wherein
the first RS in the baseline is digitized after a first baseline period, and
the first baseline period is a time period after the generation of the random numbers;
generate, after the primary executive task, a second RS in a low load (LL) and a third RS in a high load (HL), by imposing a secondary cognitive load task in a form of:
a low cognitive load inducing task on the subject, and
a high cognitive load inducing task on the subject, wherein
the secondary cognitive load task includes auditory addition of a plurality of auditory digits,
the low cognitive load inducing task includes the auditory addition of a plurality of first specific auditory digits of the plurality of auditory digits,
the high cognitive load inducing task includes the auditory addition of a plurality of second specific auditory digits of the plurality of auditory digits,
a count of the plurality of second specific auditory digits is greater than a count of the plurality of first specific auditory digits,
an auditory digit of the plurality of auditory digits is presented at a rate of 1 auditory digit per 3 seconds for the low cognitive load inducing task,
the auditory digit of the plurality of auditory digits is presented at a rate of 1 auditory digit per 4 seconds for the high cognitive load inducing task,
the low cognitive load inducing task is preceded by a first pause for a second baseline period, wherein the second baseline period is a time period after the digitization of the RS in the baseline,
the high cognitive load inducing task is preceded by a second pause for a third baseline period, wherein the third baseline period is a time period after completion of the low cognitive load inducing task,
each of the second baseline period and the third baseline period allows the subject to relax;
receive gaze data and pupillometry data associated with the subject, from an eye tracker, wherein each of the gaze data and the pupillometry data is specific data that is received during performance of both the primary executive task and the secondary cognitive load task by the subject;
extract gaze related fixation patterns from the received gaze data by separating fixation points of the gaze data and saccade points of the gaze data based on point-to-point velocities, wherein
the fixation patterns are extracted for each of the first RS in the baseline, the second RS in the LL, and the third RS in the HL,
the fixation points include a plurality of points of the gaze data having a first velocity that is lesser than a specific threshold, and
the saccade points include a second plurality of points of the gaze data having a second velocity that is equal to or greater than the specific threshold; and
compute for each of the first RS in the baseline, the second RS in the LL, and the third RS in the HL, a load index (A) by calculating a ratio of:
a product of summation of a length of repeating fixation of the fixations patterns of the extracted gaze data and a total length of random sequence, and
a total number of fixations of the gaze data, wherein
the load index indicates an effect of the secondary cognitive load task on the primary executive task, and
a value of the load index is directly proportional to the effect of the secondary cognitive load task on the primary executive task.

10. The computer program product of claim 9, wherein the computer readable program further causes the computing device to:
compute a first deviation from randomness of the first RS in the baseline, the second RS in the LL and the third RS in the HL using one or more metrics, wherein the one or more metrics includes a Coupon (Cn) test, a Gap (Gp) test, a Poker (Pk) test, a Repetitions (Rp), a Series (Sr), a Variance of digits (VD), a Digram repetitions (DR), a Cluster Ratio (CR), a Random a Number Generator (RNG), and a Turning Point index (TP), wherein
the first deviation indicates the effect of the secondary cognitive load task on the primary executive task, and
the first deviation is directly proportional to the effect of the secondary cognitive load task on the primary executive task; and
compare the received pupillometry data of the subject with the specific pupillometry data of a healthy subject to analyze the effect of the secondary cognitive load task on the primary executive task, wherein a second deviation from the specific pupillometry data indicates the effect of the secondary cognitive load task on the primary executive task.

\* \* \* \* \*